(12) United States Patent
Lee et al.

(10) Patent No.: US 10,102,346 B2
(45) Date of Patent: *Oct. 16, 2018

(54) PLAYING METHOD FOR SCREEN BASEBALL SYSTEM

(71) Applicant: REALYAGU ZONE CO., LTD., Seoul (KR)

(72) Inventors: Seung-Jin Lee, Seoul (KR); Han-Jo Kwon, Seoul (KR); Hyoung-Gon Kim, Seoul (KR)

(73) Assignee: Realyagu Zone Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/080,086

(22) Filed: Mar. 24, 2016

(65) Prior Publication Data

US 2016/0279496 A1   Sep. 29, 2016

(30) Foreign Application Priority Data

Mar. 25, 2015  (KR) .................. 10-2015-0041861

(51) Int. Cl.
*A63B 69/00* (2006.01)
*G06F 19/00* (2018.01)
(Continued)

(52) U.S. Cl.
CPC ...... *G06F 19/3481* (2013.01); *A63B 69/0002* (2013.01); *A63B 69/40* (2013.01);
(Continued)

(58) Field of Classification Search
CPC .......... A63B 69/002; A63B 2069/0008; A63B 47/002; A63B 69/40; A63B 2024/004; A63B 69/406

See application file for complete search history.

(56) References Cited

U.S. PATENT DOCUMENTS 4,442,823 A * 4/1984 Floyd .................. A63B 69/406
                                                    124/41.1
4,915,384 A * 4/1990 Bear .................. A63B 24/0021
                                                    273/454
(Continued)

FOREIGN PATENT DOCUMENTS

JP    10500592 A    1/1998
JP    10500592 A    1/1998
(Continued)

OTHER PUBLICATIONS

Japanese Notice of Allowance dated Jun. 28, 2016; Application No. 2016-061607.

(Continued)

*Primary Examiner* — Jay Liddle
(74) *Attorney, Agent, or Firm* — Heslin Rothenberg Farley & Mesiti, P.C.; George S. Blasiak, Esq.

(57) ABSTRACT

A playing method for a screen baseball system includes (a) registering a personal rank, (b) transmitting pitching information section, (c) displaying a pitching motion on a screen if a batter at an offense side presses a pitching pedal, and starting a pitching action according to the selected pitch type, (d) detecting a batting action of the batter and transmitting batting detection data to the game management unit, (e) receiving the batting detection data, converting the batting detection data into a trajectory of a batted ball, performing a simulation along the trajectory of the batted ball, and displaying an image on the screen, (f) photographing a batting image of the batter and transmitting the batting image to the game management unit, (g) receiving and transmitting batting image data and the displayed simulation information, and (h) storing the batting image and game information data.

15 Claims, 17 Drawing Sheets

(51) Int. Cl.
  *A63B 69/40* (2006.01)
  *G06Q 10/06* (2012.01)
  *G09B 19/00* (2006.01)
  *A63F 13/655* (2014.01)
  *A63F 13/573* (2014.01)
  *A63F 13/812* (2014.01)
  *A63F 13/798* (2014.01)

(52) U.S. Cl.
  CPC .......... *A63F 13/573* (2014.09); *A63F 13/655* (2014.09); *A63F 13/798* (2014.09); *A63F 13/812* (2014.09); *G06Q 10/0639* (2013.01); *G09B 19/0038* (2013.01)

(56) References Cited

U.S. PATENT DOCUMENTS

| | | | |
|---|---|---|---|
| 4,941,662 A | 7/1990 | DePerna | |
| 4,995,601 A | 2/1991 | Whitfield | |
| 5,195,744 A * | 3/1993 | Kapp | A63B 69/406 473/451 |
| 5,401,018 A * | 3/1995 | Kelly | A63B 63/00 473/140 |
| 5,443,260 A | 8/1995 | Stewart | |
| 5,868,578 A | 2/1999 | Baum | |
| 6,082,350 A | 7/2000 | Crews | |
| 6,182,649 B1 * | 2/2001 | Battersby | A63B 69/406 124/78 |
| 6,186,133 B1 * | 2/2001 | Battersby | A63B 69/406 124/78 |
| 6,186,134 B1 * | 2/2001 | Battersby | A63B 69/406 124/78 |
| 6,709,351 B2 * | 3/2004 | Hori | A63B 63/00 463/3 |
| 2001/0006063 A1 * | 7/2001 | Battersby | A63B 69/406 124/78 |
| 2001/0006064 A1 * | 7/2001 | Battersby | A63B 69/406 124/78 |
| 2001/0008755 A1 * | 7/2001 | Battersby | A63B 69/406 434/247 |
| 2001/0018912 A1 * | 9/2001 | Battersby | A63B 69/406 124/78 |
| 2003/0004017 A1 * | 1/2003 | Brown | A63B 69/406 473/422 |
| 2003/0040381 A1 | 2/2003 | Richings | |
| 2004/0088120 A1 * | 5/2004 | Kelly | A63B 24/0021 702/41 |
| 2006/0287137 A1 * | 12/2006 | Chu | A63B 47/025 473/422 |
| 2008/0300071 A1 | 12/2008 | Valaika | |
| 2009/0029754 A1 | 1/2009 | Slocum | |
| 2013/0218308 A1 | 8/2013 | Altshuler | |
| 2013/0296079 A1 | 11/2013 | Schwartz | |
| 2015/0104115 A1 | 4/2015 | Jin | |
| 2015/0350737 A1 | 12/2015 | Anderson | |
| 2016/0279526 A1 | 9/2016 | Lee et al. | |

FOREIGN PATENT DOCUMENTS

| | | |
|---|---|---|
| JP | 2001208764 A | 8/2001 |
| JP | 2005204947 A | 8/2005 |
| JP | 2005253871 A | 9/2005 |
| JP | 2006197998 A | 8/2006 |
| JP | 2006197998 A | 8/2006 |
| JP | 2009028455 A | 2/2009 |
| JP | 2012040071 A | 3/2012 |
| KR | 20010008367 A | 2/2001 |
| KR | 20010026429 A | 4/2001 |
| KR | 20070110544 A | 11/2001 |
| KR | 201300252778 A | 3/2013 |
| WO | WO2005120659 | 12/2005 |
| WO | WO2011083546 | 7/2011 |
| WO | WO2013057814 | 4/2013 |

OTHER PUBLICATIONS

Japanese Office Action dated Jul. 12, 2016; Application No. JP2016-061645.

Non-Final Office Action for U.S. Appl. No. 15/080,022 filed Mar. 24, 2016, dated Oct. 24, 2017.

Applicant's response to Non-Final Office Action for U.S. Appl. No. 15/080,022, filed Mar. 24, 2016, dated Jan. 23, 2018.

Final Office action for U.S. Appl. No. 15/080,022, filed Mar. 24, 2016, dated Mar. 30, 2018.

Applicant's Response to Final Office action for U.S. Appl. No. 15/080,022, filed Mar. 24, 2016, dated Jun. 29, 2018.

* cited by examiner

138

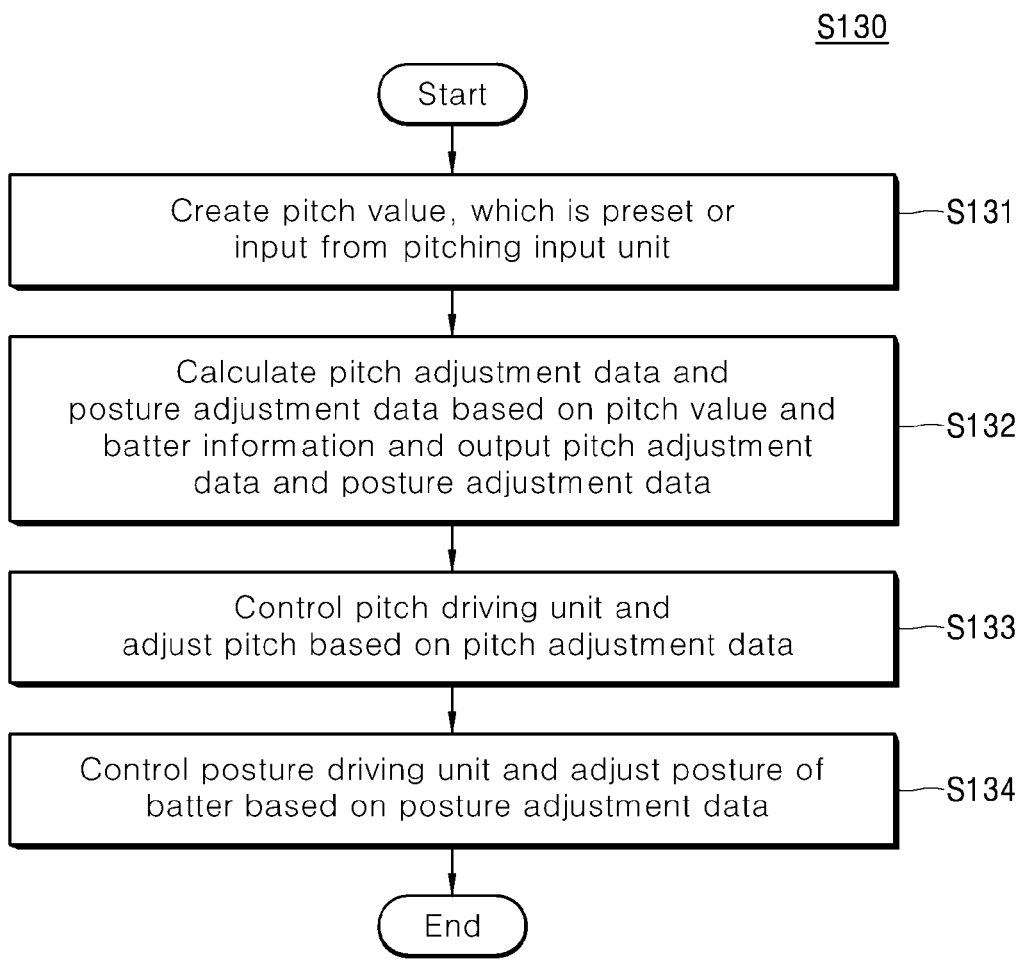

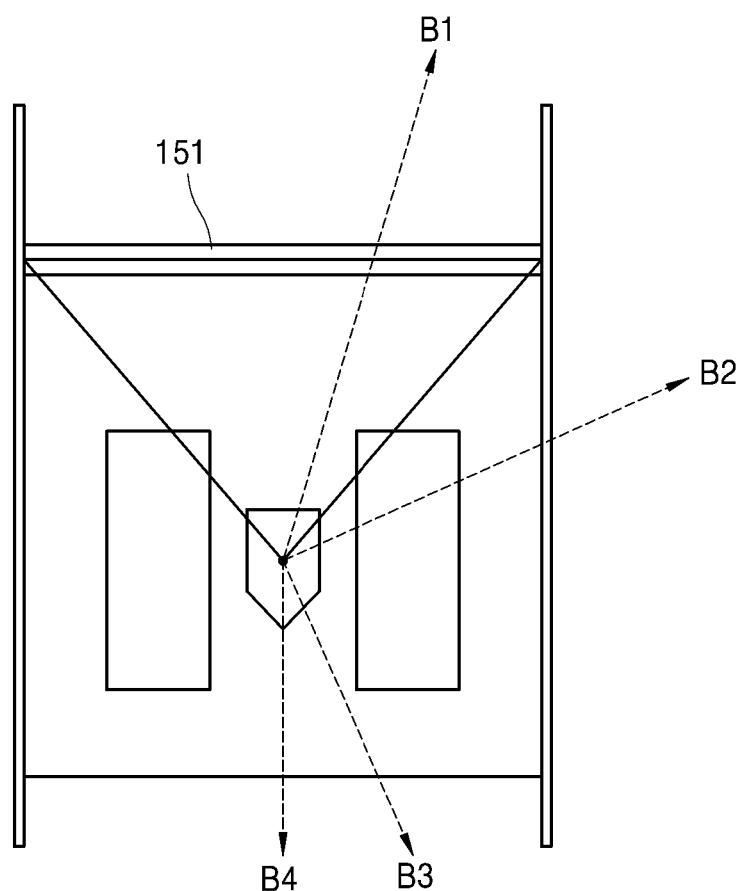

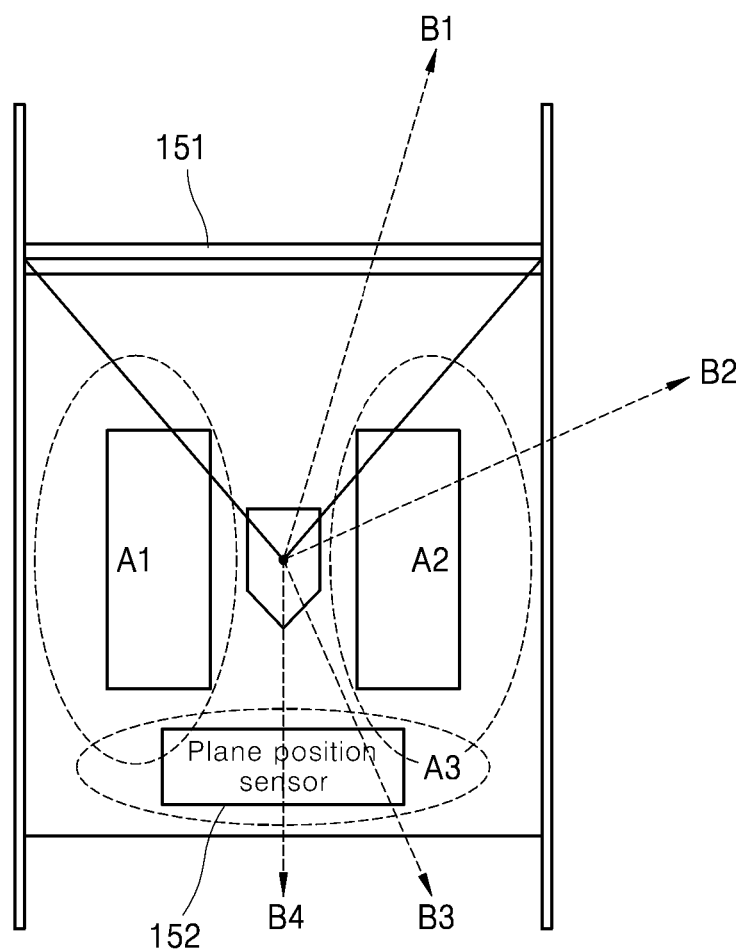

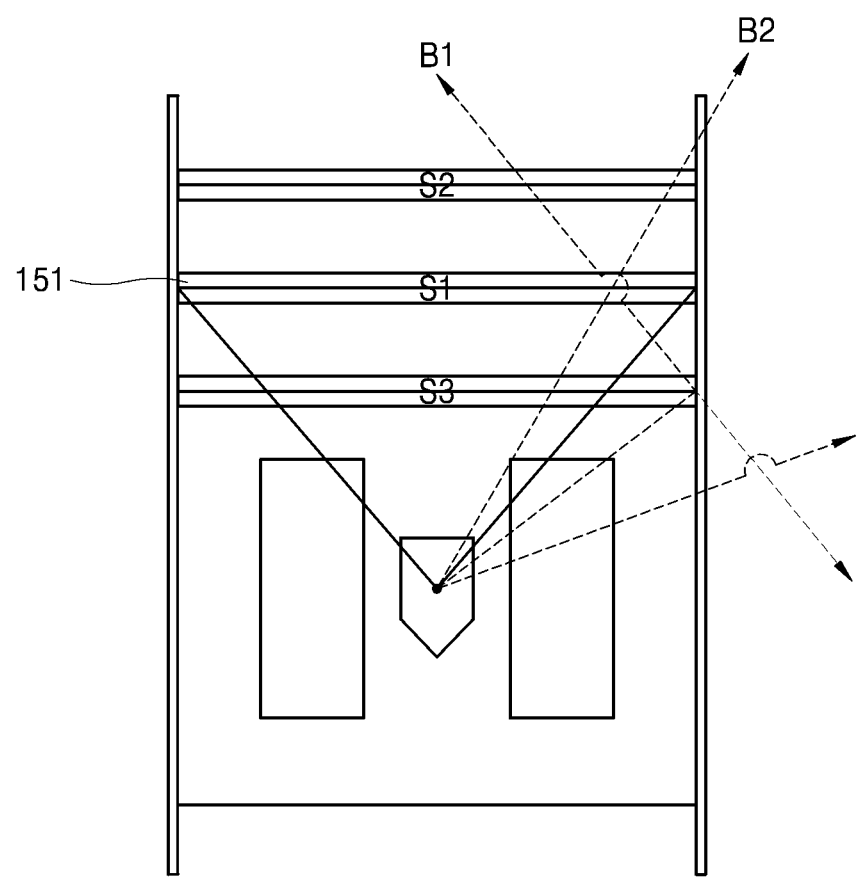

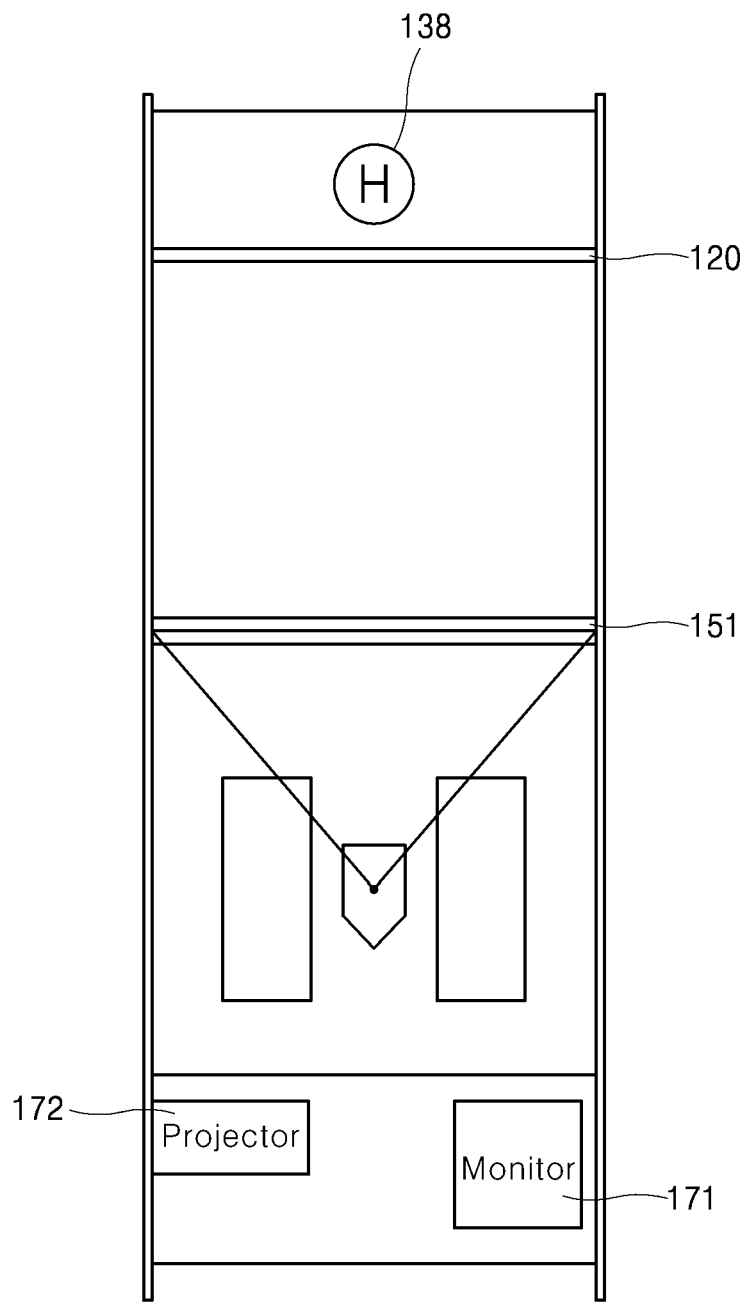

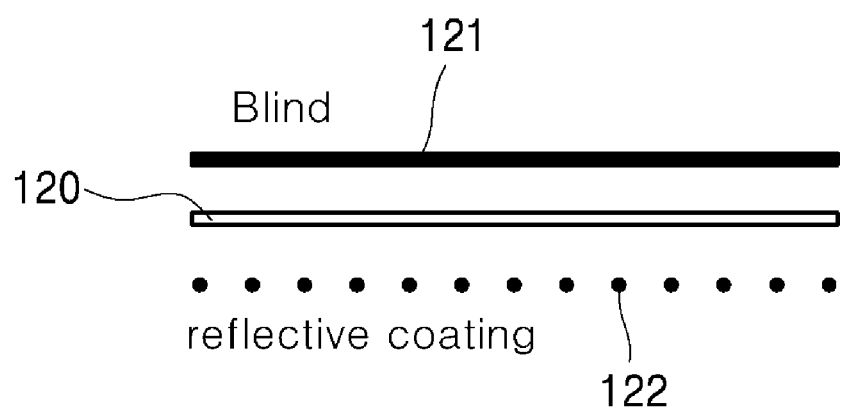

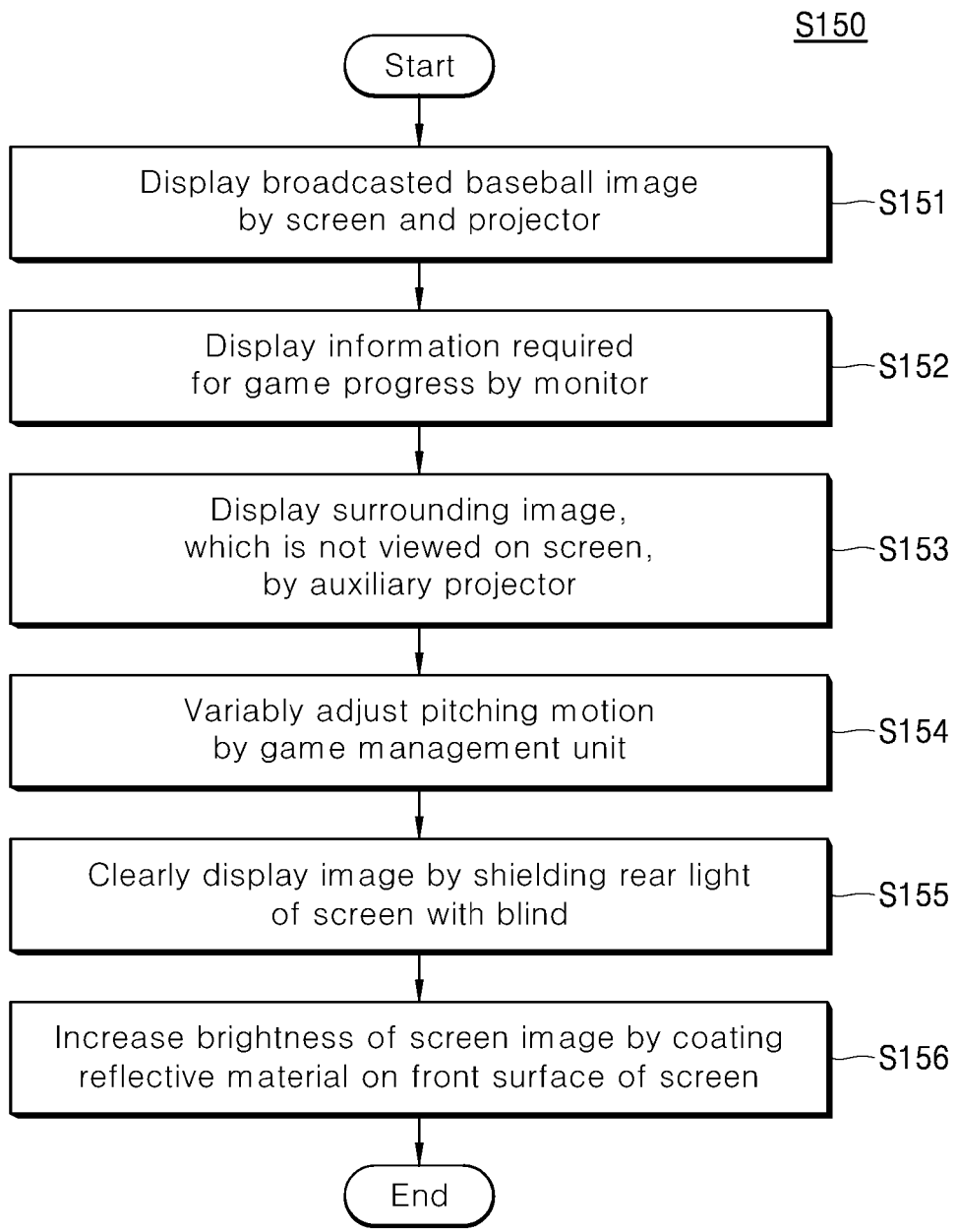

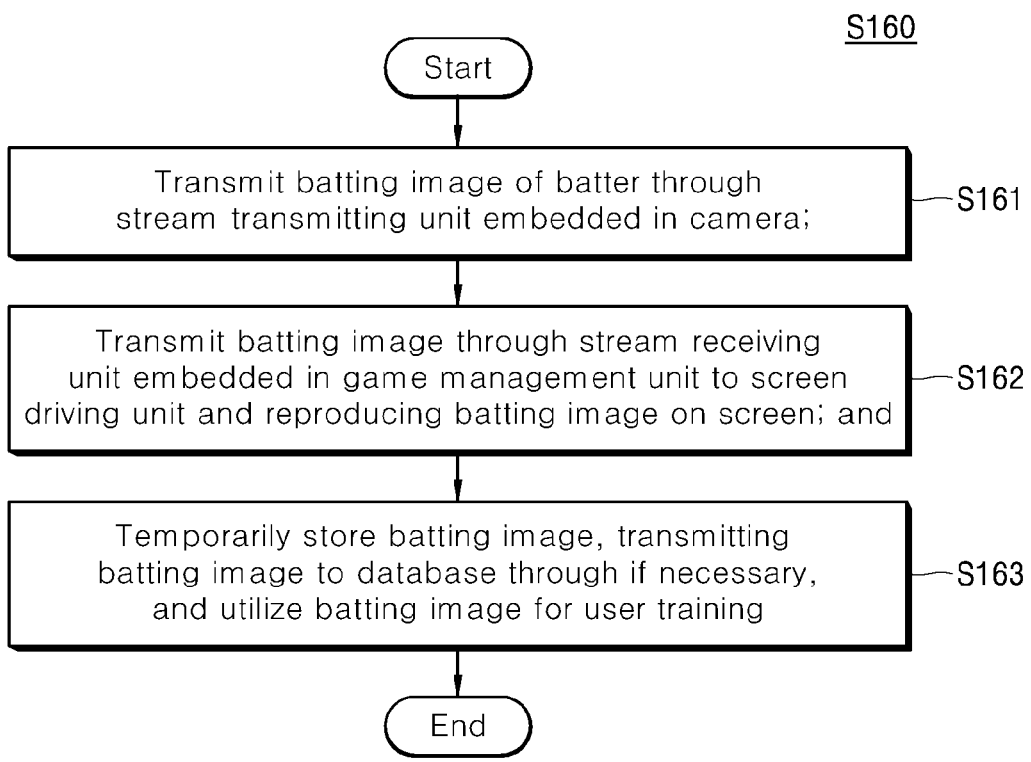

PLAYING METHOD FOR SCREEN BASEBALL SYSTEM

CROSS-REFERENCE TO RELATED APPLICATION

This application claims priority to Korean Patent Application No. 10-2015-0041861 filed on Mar. 25, 2015, and all the benefits accruing therefrom under 35 U.S.C. § 119, the contents of which is incorporated by reference in its entirety.

BACKGROUND OF THE INVENTION

1. Field of the Invention

The present invention relates to a playing method for a screen baseball system, and more particularly to a playing method for a screen baseball system, enabling users to variously enjoy baseball without a difference in level between the users and temporal and spatial limitations, capable of moving a ball with reality along a predetermined trajectory according to pitching or batting in a virtual baseball field, and capable of improving game capability of a user by utilizing game information for a user training program.

2. Description of the Related Art

In general, a pitcher casts a ball, a catcher receives the ball, and a batter hits the ball to score a point in a baseball.

In the batting practice of a batter, if one person casts a ball, the batter may bat the ball. In addition, the batter may carry out the batting practice by batting a ball fling and coming using a baseball batting practice device to periodically shoot a baseball.

Further, if a user is a beginner, a woman, or a child, the user may bat a tee-ball fixed to a support positioned at a predetermined height by a bat.

As described above, since baseball requires some persons and a relatively large space, an ordinary person has limitations of human power, time, and a space in freely interesting the baseball.

In order to solve the problem, conventionally, batting cages have been provided with pitching machine. In the case of the batting cages, it may be substantially impossible for a user to select a pitch type or cope with various conditions.

Further, since a game depending on batting progresses, reality and interesting are remarkably degraded in "strike", "out", or "scoring".

Meanwhile, recently, indoor golf driving ranges or screen golf driving ranges having maximized spatial utilization have been increased to allow a user to practice golf as one of indoor sports using a ball.

In the case of a typical screen golf system, a predetermined projection apparatus projects images on the front surface of a screen and reproduces the images, and a batter fixedly places a golf ball to a predetermined position and hits the golf ball into a virtual space projected onto the screen to progress a game.

However, in the case of golf, since only a hitter is required, and a ball to be hit is stopped, a game may progress or an image may be realized without a serious problem. On the other hand, in the case of baseball, a virtual ballpark must be formed, a pitcher and a batter are required, and a ball must be moved with reality along a trajectory of a pitched ball or a batted ball. Accordingly, there is a limitation when a screen golf system is applied to baseball.

Further, in the case of baseball, factors to determine "strike" or "ball" are required, various offensive and defensive actions are optionally and dynamically made and a score is dynamically calculated. Accordingly, the baseball basically differs from the golf in game factors, so that the application of the screen golf system to the baseball is actually impossible.

As patent documents for prior arts, there are KR 10-2007-0110544 A and JP2005-204947 A.

SUMMARY OF THE INVENTION

An object of the present invention is to provide a playing method for a screen baseball system, enabling ordinary people to easily select a pitch of a ball to be pitched or various game conditions, capable of variously adjusting determination of "strike" or "ball", options in various offensive and defensive actions, or a point calculating scheme beyond a game depending on batting, and enabling users not only to share the information of players and a game simulation in real time on line between regions geographically spaced apart from each other, but also to store batting images during a game to utilize the batting images for a user training program and a character development program.

The objects of the present invention are not limited to the above-mentioned objects, and other objects will be clearly understood from the following description by those skilled in the art.

In order to accomplish the above objects, there is provided a playing method for a screen baseball system, which includes (a) registering a personal rank by a game management unit, (b) transmitting pitching information to a pitching machine section as a pitch type of a ball to be pitched is selected by a defense side user, (c) displaying a pitching motion on a screen if a batter at an offense side presses a pitching pedal, and starting a pitching action according to the selected pitch type by the pitching machine section, (d) detecting a batting action of the batter by a batting detection unit and transmitting batting detection data to the game management unit, (e) receiving the batting detection data, converting the batting detection data into a trajectory of a batted ball, performing a simulation according to the trajectory of the batted ball, and displaying an image on the screen by the game management unit, (f) photographing a batting image of the batter and transmitting the batting image to the game management unit by a game photographing unit, (g) receiving batting image data and the displayed simulation information and transmitting the batting image data and the simulation information to a game server and a database by an online communication unit, and (h) storing the batting image and game information data by the database such that the batting image and the game information data are utilized for a user training program and a character development program.

The playing method further includes (i) transmitting the simulation information and the batting image data, which are displayed, to a shop, where the defense side user is positioned, in real time by the game server to play a game on line, if the defense side user is another user positioned in a geographically remote region.

The registering of the personal rank includes issuing a registration card having the personal rank and member subscription information of a user, and registering the personal rank through a reader to read the registration card.

The registering of the personal rank includes inputting the personal rank and member subscription information of the user using an application of a portable terminal, and registering the personal rank together with the application through a short-range communication function of the portable terminal.

The transmitting of the pitching information includes selecting the pitch type of the ball to be pitched through a keypad or a joystick to prevent the pitching information from leaking to the offense side.

The displaying of the pitching motion includes a pitch data calculation step of outputting a pitch value, which is created based on a preset value as the pitching information is received, a pitch value input into a pitching input unit, a pitch adjustment data corresponding to a strike zone based on information of a batter, and a posture adjustment data, a pitch adjustment step of receiving the pitch adjustment data to control a pitch driving unit and to adjust a pitch of a ball to be pitched, and a posture adjusting step of receiving the posture adjustment data to control a posture driving unit such that a posture of the batter is adjusted.

The displaying of the pitching motion includes determining the pitch type of the ball to be pitched depending on rotational speeds of three wheels by pitching machine having the three wheels pushing the ball by rotating forward.

The displaying of the pitching motion includes previously storing an adjustment value for a specific pitch into an embedded memory device of the pitching machine section by considering that each shop has a different revolution of pitching machine and a different distance between the pitching machine and a batter box The detecting of the batting action includes detecting coordinate data of the batted ball as a plurality of front detection sensors are mounted at a position where a ballpark makes contact with an extension line of a base, and at a front or a rear of the position, detecting a strike ball, which fails to be batted, and a foul ball as a plurality of plane position sensors are positioned at left and right batter boxes and a catcher region, and removing a shadow part from the trajectory of the batted ball and detecting change of a movement direction of the batted ball at a batting point as a camera sensor is mounted in a home plate region.

The receiving of the batting detection data includes manually adjusting a defensive position according to at least one of a batter characteristic, a runner situation, and a score situation by the defense side user, and manually adjusting a runner motion according to at least one of the runner situation and the score situation by the offense side.

The receiving of the batting detection data includes displaying a broadcasted baseball image to represent a motion of a player on the screen through a projector, displaying information required for game progress on a monitor mounted in a batter waiting room, and displaying a surrounding image, which is not viewed on the screen, on a wall surface through an auxiliary projector.

The receiving of the batting detection data includes freely adjusting an appearance of a pitcher depending on a distance between the screen and a batter box by the game management unit, and shielding light of a rear surface of the screen with a blind, and coating a reflective material on a front surface of the screen.

The photographing and transmitting of the batting image of the batter include transmitting the batting image of the batter through a stream transmitting unit embedded in a camera, transmitting the batting image through a stream transmitting unit embedded in the game management unit to a screen driving unit and reproducing the batting image on the screen, and temporarily storing the batting image, transmitting the batting image to the database through the stream transmitting unit if necessary, and utilizing the batting image for the user training program and the character development character.

The receiving and the transmitting of the batting image data and the displayed simulation information are performed using one of a wired communication network, a short-range communication network, and an Internet network.

The transmitting of the simulation information and the batting image data includes inputting an available game schedule in an individual unit of a user or a team unit by the game server, and providing the available game schedule to the another user in the remote place.

Details of other embodiments are included in the detailed description and accompanying drawings.

The advantages, the features, and schemes of achieving the advantages and features of the present invention will be apparently comprehended by those skilled in the art based on the embodiments, which are detailed later in detail, together with accompanying drawings. The present invention is not limited to the following embodiments but includes various applications and modifications. The embodiments will make the disclosure of the present invention complete, and allow those skilled in the art to completely comprehend the scope of the present invention. The present invention is only defined within the scope of accompanying claims.

As described above, according to the present invention, ordinary people can easily select a pitch of a ball to be pitched or various game conditions to freely enjoy baseball without a limitation such as the difference in level between users.

Further, determination of "strike" or "ball", options in various offensive and defensive actions, or a point calculating scheme can be variously adjusted beyond a game depending on batting. In addition, a ball is movable with reality along a predetermined trajectory according to pitching or batting in a virtual baseball field, so that the reality and interesting can be improved.

In addition, users can play a game even in mutually different regions by sharing the information of players and a game simulation in real time on line between regions geographically spaced apart from each other. Accordingly, the users can enjoy baseball without temporal and spatial limitations. The batting posture of the user is corrected through the character development program based on the batting images in the game, so that the user can improve a game capability.

BRIEF DESCRIPTION OF THE DRAWINGS

FIG. 4 is a flowchart showing a part of an operation of a pitching step in the playing method for the screen baseball system according to the present invention.

FIGS. 5A through 5D show views to explain the operation of a batting detection unit in a screen baseball system shown in FIG. 1

FIGS. 7A through 7C show views to explain the operation of a screen driving unit in the screen baseball system shown in FIG. 1.

FIG. 8 is a flowchart showing a part of an operation of a screen driving step in the playing method for the screen baseball system according to the present invention.

FIG. 10 is a flowchart showing a part of an operation of a screen driving step in the playing method for the screen baseball system according to the present invention.

DETAILED DESCRIPTION OF THE INVENTION

Hereinafter, an exemplary embodiment of the present invention will be described in detail with reference to accompanying drawings.

The terminology and words used herein and accompanying claims should be not interpreted as the meanings of commonly used dictionaries, but interpreted as having meanings according to the technical sprit of the present invention on the principle that the concepts of the terminology and the words can be defined by the inventor in order to explain the present invention in the best mode.

Throughout the whole specification, when a predetermined part "includes" a predetermined component, the predetermined part does not exclude other components, but may further include other components unless the context clearly indicates otherwise In addition, the terms "part", "machine", "module", "device", or "step" refer to units to process at least one function or operation, and is realized by hardware or software, or the combination of the hardware and the software.

In the following description, a portable terminal refers to a smart phone, a personal digital assistant (PDA), a portable multimedia player, or a smart pad which can be aided by a computer through Internet communication.

Figure 1:
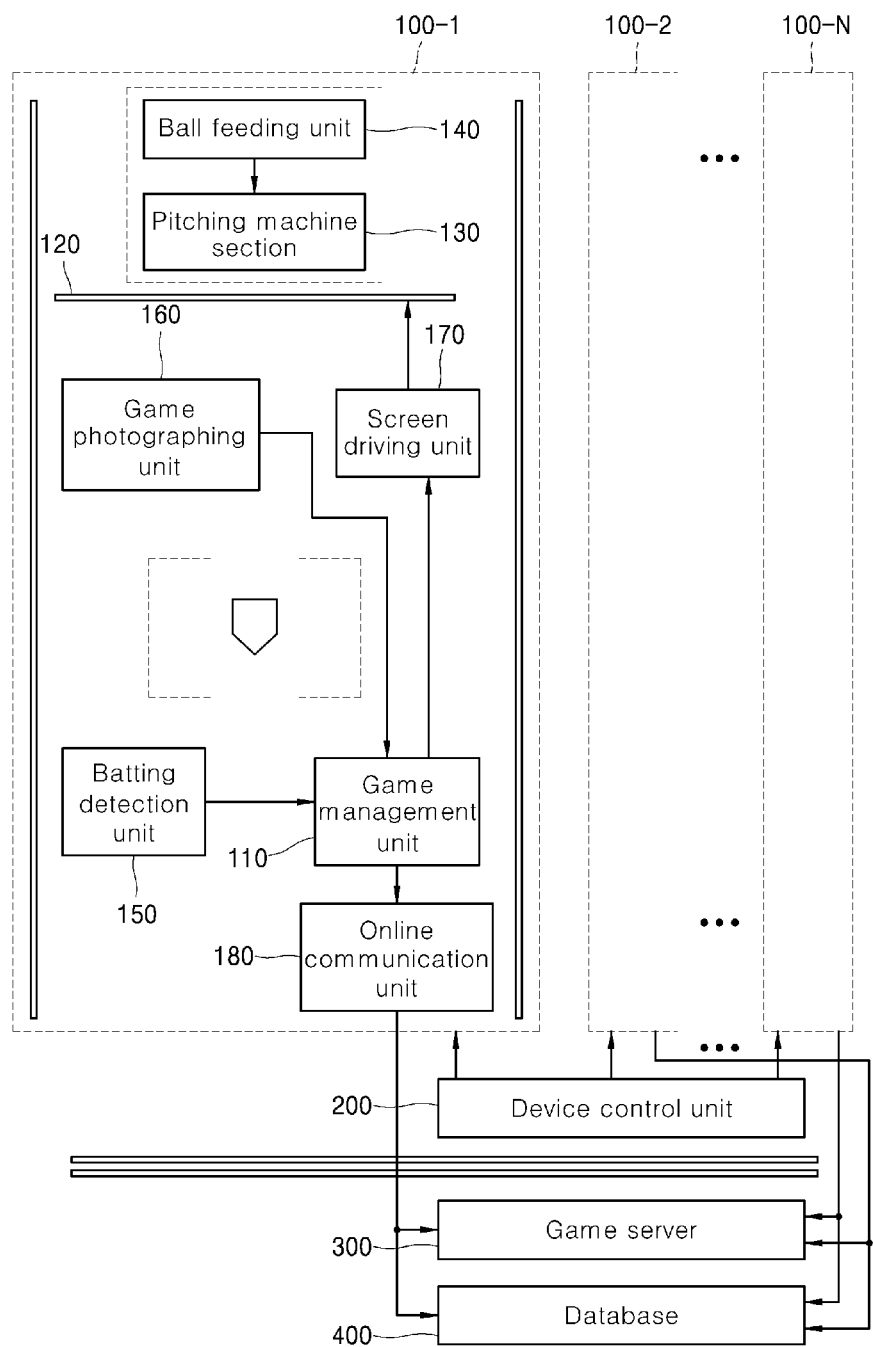
FIG. 1 is a schematic view showing a baseball system to realize a playing method for a screen baseball system according to the present invention.

FIG. 1 is a schematic view showing the structure of a baseball system to realize a playing method for a screen baseball system according to the present invention, and the screen baseball system includes a plurality of screen baseball devices 100-1 to 100-N, a device control unit 200, a game server 300, and a database 400.

Each of the screen baseball devices 100-1 to 100-N includes a game management unit 110, a screen 120, a pitching machine section 130, a ball feeding unit 140, a batting detection unit 150, a game photographing unit 160, a screen driving unit 170, and an online communication unit 180.

Hereinafter, the function of each component of the screen baseball system to realize the playing method for the screen baseball system according to the present invention will be described with reference to FIG. 1.

The game management unit 110 registers a personal rank of a user, performs a simulation according to the trajectory of a batted ball, which is obtained by receiving and converting batting detection data, displays a game image on a screen 120 through the screen driving unit 170, and variously adjusts the appearance of a pitcher depending on the distance between the screen 120 and a box of a batter.

The pitching machine section 130 receives a ball from the ball feeding unit 140 and automatically or manually pitches the ball based on information on a pitch type selected by a user positioned at a defense side.

The batting detection unit 150 includes a plurality of front detection sensors, a plurality of plane position sensors, and a camera sensor to detect coordinate data of a batted ball, a strike ball which fails to be batted, and a foul ball, to remove a shadow part from the trajectory of the batted ball, and detects the change of a movement direction of the batted ball at a batting point.

The game photographing unit 160 photographs the batting image of the user and transmits the batting image of the user to a game management unit 110.

The screen driving unit 170 receives the batting image photographed by the game photographing unit 160 and a simulation image of the game management unit 110 and reproduces the batting image and the simulation image on the screen 120.

The online communication unit 180 transmits simulation information and batting image data displayed on the screen 120 to the game server 300 and the database 400.

The device control unit 200 integrally monitors and controls a plurality of screen baseball devices 100-1 to 100-N.

The game server 300 transmits the simulation information and the batting image data displayed on the screen 120 to another user positioned at a remote place in real time so that a baseball game progresses on line.

The database 400 receives a batting image and game information data from the online communication unit 180 and stores the batting image and the game information data therein so that the batting image and the game information are utilized for a user training program and a character development program.

Figure 2:
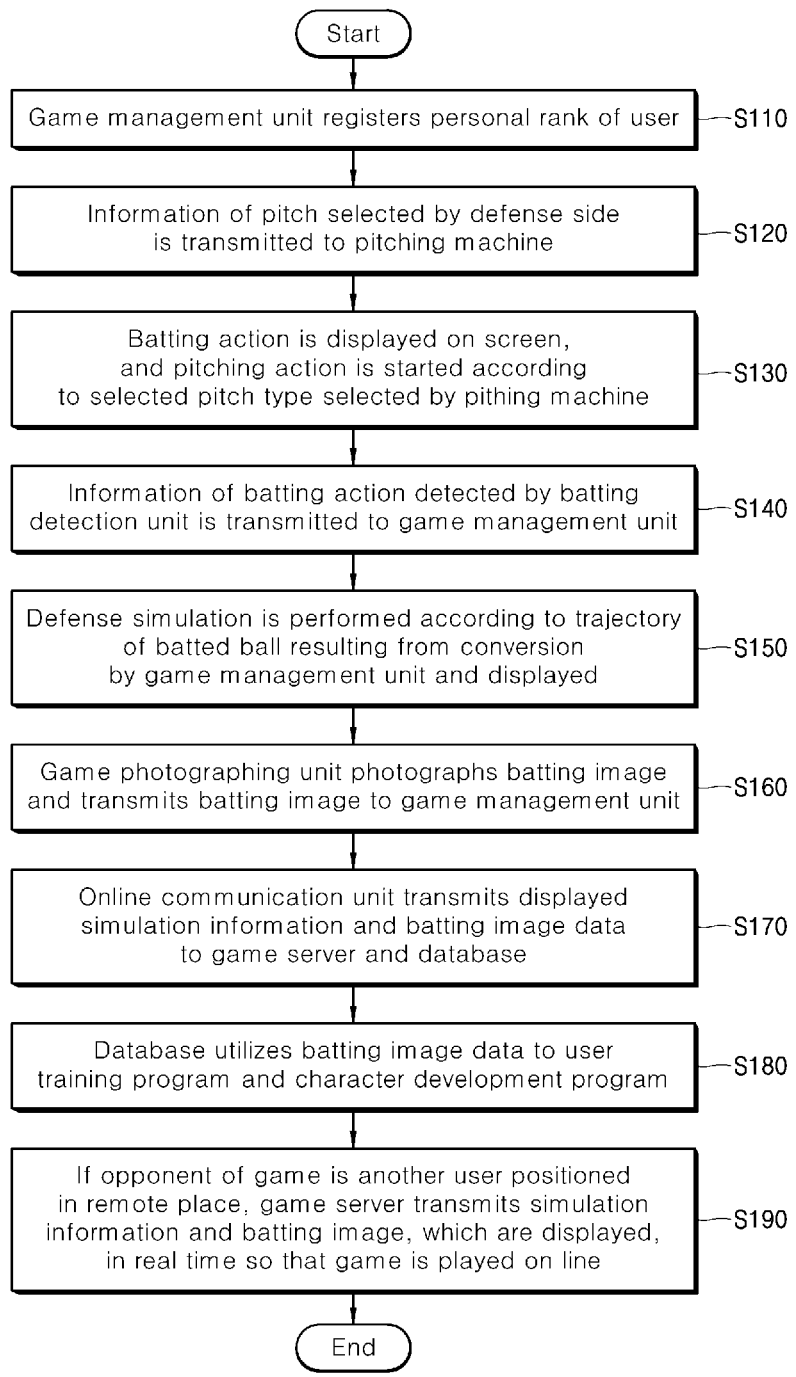
FIG. 2 is a flowchart showing the overall operation of a playing method for a screen baseball system according to the present invention.

FIG. 2 is a flowchart showing the overall operation of the playing method for the screen baseball system according to the present invention.

Hereinafter, the overall operation of the playing method for the screen baseball system according to the present invention will be described with reference to FIGS. 1 and 2.

The game management unit 110 registers the personal rank of a user and opens a game (S110).

If the batter is at bat, the game management unit 110 checks the personal rank of the batter based on registered user information.

If a user positioned at a defense side takes a basic defense operation, for example, selects a pitch type, the information of the pitch is transmitted to the pitching machine section 130 (S120).

If the batter presses a pitch pedal provided in a batter box, a batting action is displayed on the screen 120, and a pitching action is started according to the selected pitch type (S130).

If the batter bats a ball, the information of the batting action detected by the batting detection unit 150 is transmitted to the game management unit 110 (S140), and analyzed as the trajectory of an arch. The game simulation is performed based on the analysis, and the game image is displayed on the screen 120 (S150).

In this case, the game photographing unit 160, which is mounted on an upper portion of a left wall or a right wall in front of the batter, photographs the batting action of the batter, and transmits the batting image to the game management unit 110 (S160).

The same procedure is applied to a next batter, and the game is continuously played according to a baseball rule.

The progressing procedure of the game is transmitted to the game server 300 and the database 400 through the online communication unit 180 (S170).

The database 400 receives the batting image and the game information data from the game management unit 110 and stores the batting image and the game information data therein so that the batting image and the game information are utilized for the user training program and the character development program (S180).

Meanwhile, if an opponent of a game is another user positioned in a remote place, the game server 300 transmits the simulation information and the batting image, which are displayed, to a game shop, in which the opponent is positioned, in real time so that the game may be played on line (S190).

For example, when a plurality of users want make a team in a shop C and play a game together with another team, and a desirable opposite team is located at another shop D, the game server 300 displays simulation information and batting image data, which are displayed in the shop C, on a monitor or screen of the game management unit 110 in the shop D as if both teams play a game in one place.

Hereinafter, a game management step and a control step in a screen baseball system according to the present invention will be described with reference to FIGS. 1 and 2.

Operation in Game Management Step

The game management unit 110 is provided in the form of a personal computer (PC) and located adjacent to the batter box, and includes a keyboard, a mouse, a monitor, or a touch screen.

The game management unit 110 registers a user to be first at bat in each team. In this case, the game management unit 110 registers the user in such a manner that personal rank of the user is applied to and reflected on the game.

In order to simplify user registration, additional registration cards (a bar code or an RF card) having the personal rank and the member subscription information of the user may be issued and a relevant reader may be mounted as an input device.

In addition, as the portable terminal is extensively used, the personal rank and the member subscription information of the user are input through an application of the portable terminal, and the application is executed through a short-range communication function of the portable terminal so that the personal rank of the user may be registered.

The game management unit 110 allows a defense team to select a pitch type of a ball to be pitched by the pitching machine section 130.

In this case, to prevent pitching information from leaking to an offense side, an additional input device provided in the form of a keypad may be equipped.

Generally, in a baseball game, a defensive position can be dynamically changed according to a batter characteristic, a runner situation, and a score situation. The game management unit 110 allows the selection of the defensive position through a basic input device or an additional keypad.

The offense side changes the motion of a runner (run-and-hit, or hit-and-run) according to the runner situation and the score situation, which serves as an important factor to increase the game participation of the user. Accordingly, the game management unit 110 may set the motion of the runner through the basic input device and the additional input device.

The keypad or the additional input device not only includes a button set including a small number of buttons, but also include a game manipulation device such as a joystick and an application installed in the portable terminal.

The batting data detected by the batting detection unit 150 are changed to the trajectory of the ball, and the game is simulated so that the defending procedure is automatically performed according to the trajectory of the ball and the game situation.

Baseball is called a record game so that each game element serves as an important factor. Accordingly, the information of a present game becomes important basic information when a next game is played.

Accordingly, the information of the present game is subject to a predetermined process for the storage in the database 400 to be described.

In addition, the communication scheme is not limited to a wired scheme, but includes a processing scheme through an application based on a short-range communication network in a smart phone.

Operation of Game Server and Database

The game server 300 allows the game record (winning percentage and batting average) of an individual and a relevant team.

In addition, both teams may play a game not only in one place, but also in mutually different regions by sharing the information of players and a game simulation in real time on line between regions geographically spaced apart from each other.

Further, the game server 300 inputs an available game schedule in an individual unit or a team unit, or allows a user to check the available game schedule of another person. Accordingly, the game server 300 controls a game match so that the user may search for a ballpark together with an opponent to play a game, and may easily find an opponent to play a game even if there is no opponent.

Accordingly, more conveniently, a user may play a game together with an opponent in one place, and play an online game together with an opponent in a different place.

Meanwhile, if the superiority or the inferiority of a player is determined based on a physical advantage or a physical disadvantage, the player is avoided as an opponent. Accordingly, in order to overcome this, the game server 300 constructs a user training program and a character development program to be reflected on the game simulation.

The above function is not provided for a user through a specific input/output device. In other words, only if the user basically accesses the Internet, the above function may be provided in various forms such as a web browser or an application.

Figure 3A:
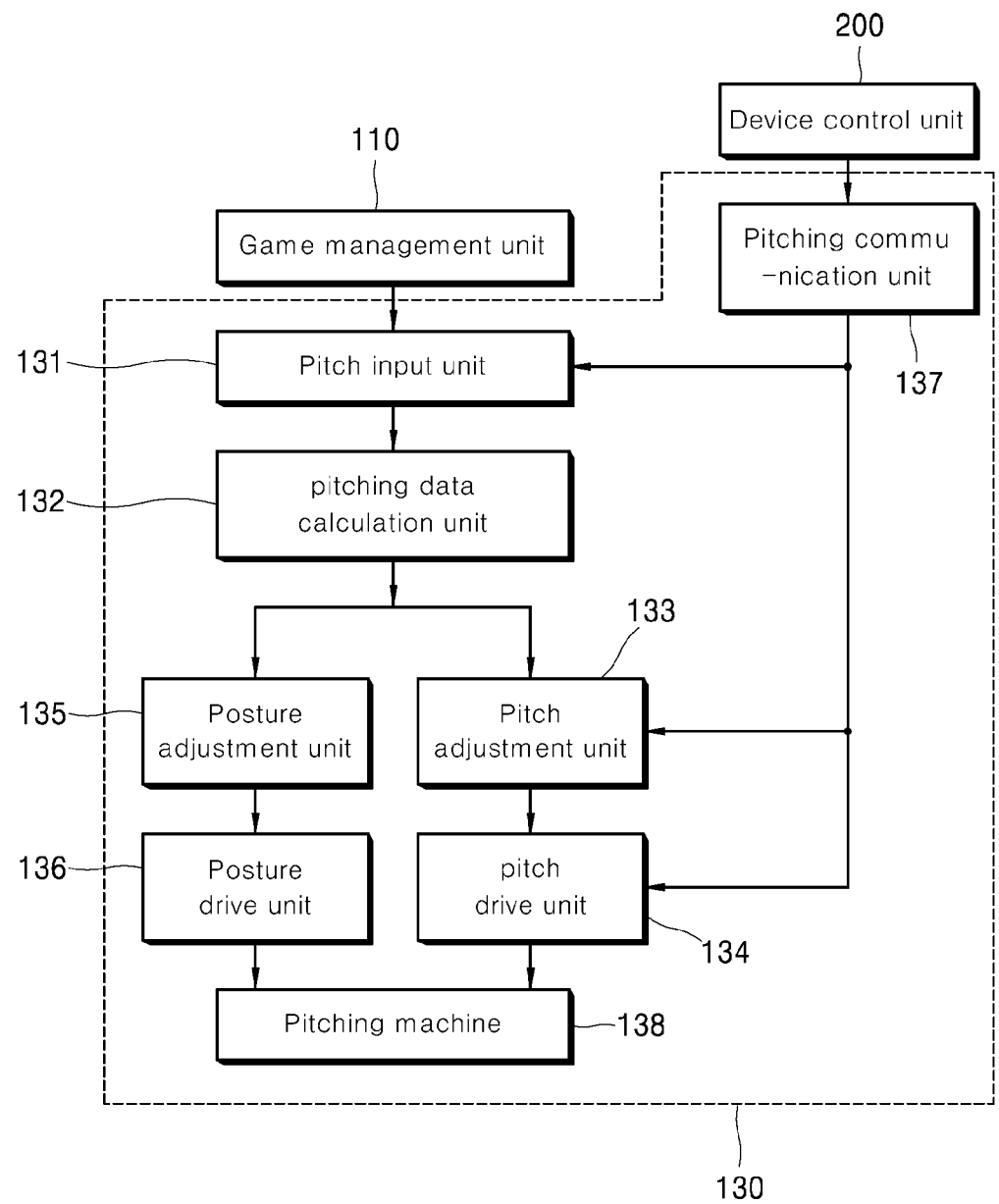
FIGS. 3A and 3B show views to explain the operation of a pitching machine section in the screen baseball system shown in FIG. 1.
Figure 3B:
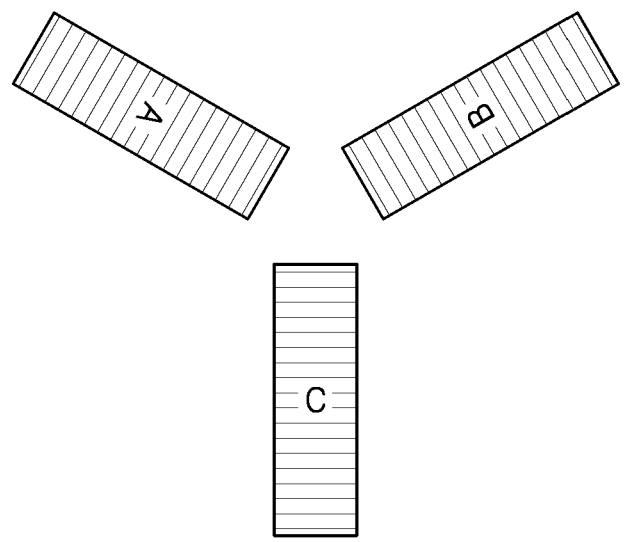

FIGS. 3A AND 3B are a view to explain the operation of the pitching machine section 130 in the screen baseball system shown in FIG. 1. The screen baseball system includes the game management unit 110, the pitching machine section 130, and the device control unit 200. The pitching machine section 130 includes a pitching input unit 131, a pitching data calculation unit 132, a pitch adjustment unit 133, a pitch drive unit 134, a posture adjustment unit 135, a posture drive unit 136, a pitching communication unit 137, and a pitching machine 138.

FIG. 4 is a flowchart showing a part of an operation of a pitching step in the playing method for the screen baseball system according to the present invention.

Hereinafter, the operation of a pitching step in the screen baseball system according to the present invention will be described with reference to FIGS. 1 to 4.

Operation in Pitching Step

As shown in FIG. 3A, the pitch of a ball to be pitched, which is selected by the defense side on the game management unit 110, and the personal rank of a batter, and pitching data of the batter, such as the height of the batter, which are registered in the game photographing unit 160, are transmitted to the pitching input unit 131 through serial communication, LAN, or Internet.

The pitching data calculation unit 132 receives the pitching data from the game management unit 110 to generate a pitch value, which is preset or input from the pitching input unit 131 (S131). Data for pitch adjustment and posture adjustment are calculated and output corresponding to a strike zone using the pitch value and the information of the batter (S132).

The pitch adjustment unit 133 receives the data for pitch adjustment from the pitch data calculation unit 132 to control the pitch drive unit 134 so that the pitch is adjusted. Accordingly, the pitching data 138 performs a pitching action corresponding to the input pitching data (S133).

The posture adjustment unit 135 receives the data for posture adjustment from the pitching data calculation unit 132 to control the posture drive unit 136 and to adjust the pitching machine 138, so that the pitching machine 138 performs the pitching action corresponding to the input pitching data.

The pitching input unit 131, the pitch adjustment unit 133, and the posture adjustment unit 135 include additional input devices such as a keypad or a volume controller. Accordingly, if there is no additional pitching data input signal from the game management unit 110, or the pitching machine 138 is set to be manually adjusted, the pitching machine 138 may simultaneously pitch balls having a specific pattern.

The pitching machine 138 may be manually adjusted by integrally monitoring and controlling a plurality of pitching machines 138 by the device control unit 200 through the pitching communication unit 137.

As shown in FIG. 3B, the pitching machine is provided in the form of three wheels, and a ball is pushed as the three wheels A, B, and C are rotated forward. According to the rotational speeds of the three wheels A, B, and C, the pitch type of the ball is determined.

In other words, if the three wheels A, B, and C have the same rotational speeds, a ball in the form of a fastball is pitched. In this case, the speed of the ball is determined in proportion to the revolutions of the wheels A, B, and C.

If the rotation of the wheel C is adjusted in the state that the rotational speeds of the wheels A and B are equal to each other, the ball is pitched in the form of a forkball, in which the drop of the ball is sharpened or dulled.

Similarly, if the revolutions of the wheels A and B are adjusted in the state that the rotational speeds of the wheels A and B are equal to each other as that of the wheel C, the ball is pitched in the form of a curveball.

In an actual operation in a shop, the revolutions of the pitching machine are varied depending on the distance between the pitching machine and the batter box. Accordingly, it is significantly difficult to individually adjust the revolutions every time according to pitches. Therefore, preferably, the pitching machine section 130 previously stores an adjustment value for a specific pitch in an embedded memory device (for example, EPROM, or RAM), and uses the adjustment value.

FIGS. 5A through 5D show views to explain the operation of the batting detection unit 150 in a screen baseball system shown in FIG. 1, and the batting detection unit 150 includes a front detection sensor 151, a plane position sensor 152, and a camera sensor 153.

Figure 6:
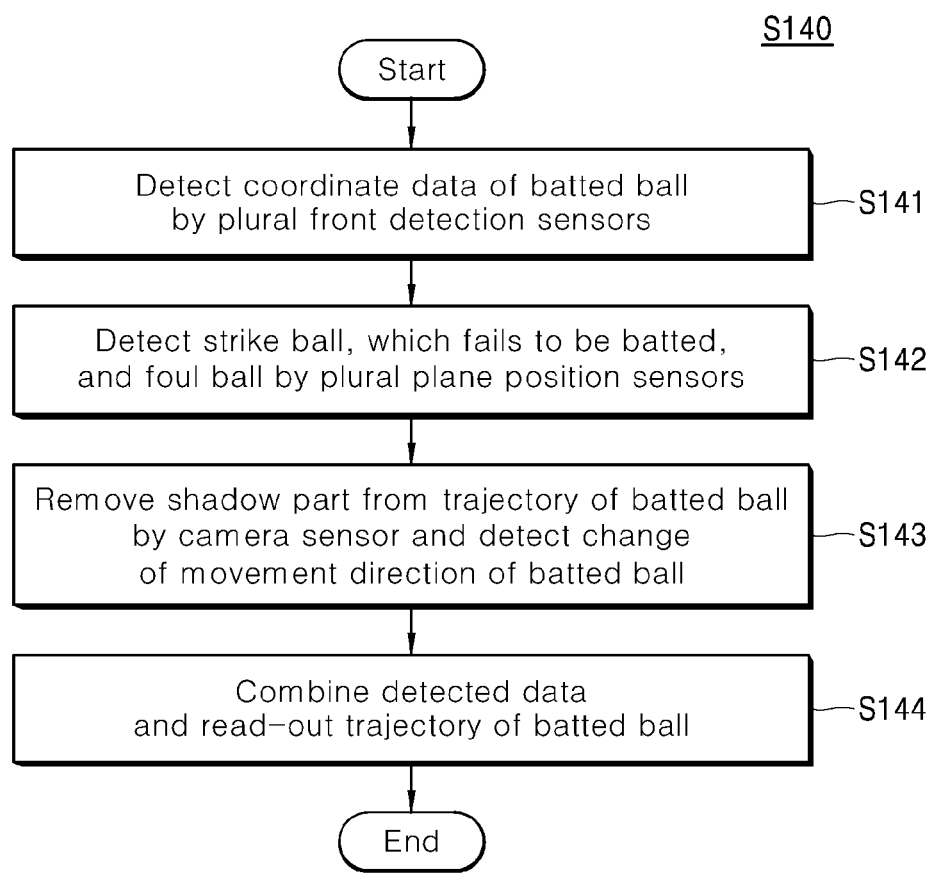
FIG. 6 is a flowchart showing a part of an operation of a batting detection step in the playing method for the screen baseball system according to the present invention.

FIG. 6 is a flowchart showing a part of an operation of a batting detection step in the playing method for the screen baseball system according to the present invention.

Hereinafter, the operation of the batting detection step in the screen baseball system according to the present invention will be described with reference to FIGS. 1 to 6.

Operation in Batting Detection Step

As shown in FIG. 5A, although the front detection sensor 151 may detect horizontal and vertical coordinate data of the batted ball to detect the trajectory of the batted ball (S141), the front detection sensor 151 may detect only the trajectory B1 of the batted ball according to the mounting position of the front detection sensor 151, and may not detect trajectories B2, B3, and B4 of the batted ball, which may generate shadow parts.

Accordingly, it may be difficult to distinguish between the strike ball, which fails to be batted, and a batted ball (foul ball) which does not pass through the front detection sensors, so that the reality may be degraded in playing a game.

In order to overcome this problem, according to the present invention, as shown in FIG. 5B, additional plane position sensors 152 (for example, ultrasonic sensor) are placed at left and right batter boxes A1 and A2 and a catcher region A3 to detect the trajectories of the batted ball B2, B3, and B4 (S142).

Figure 5C:
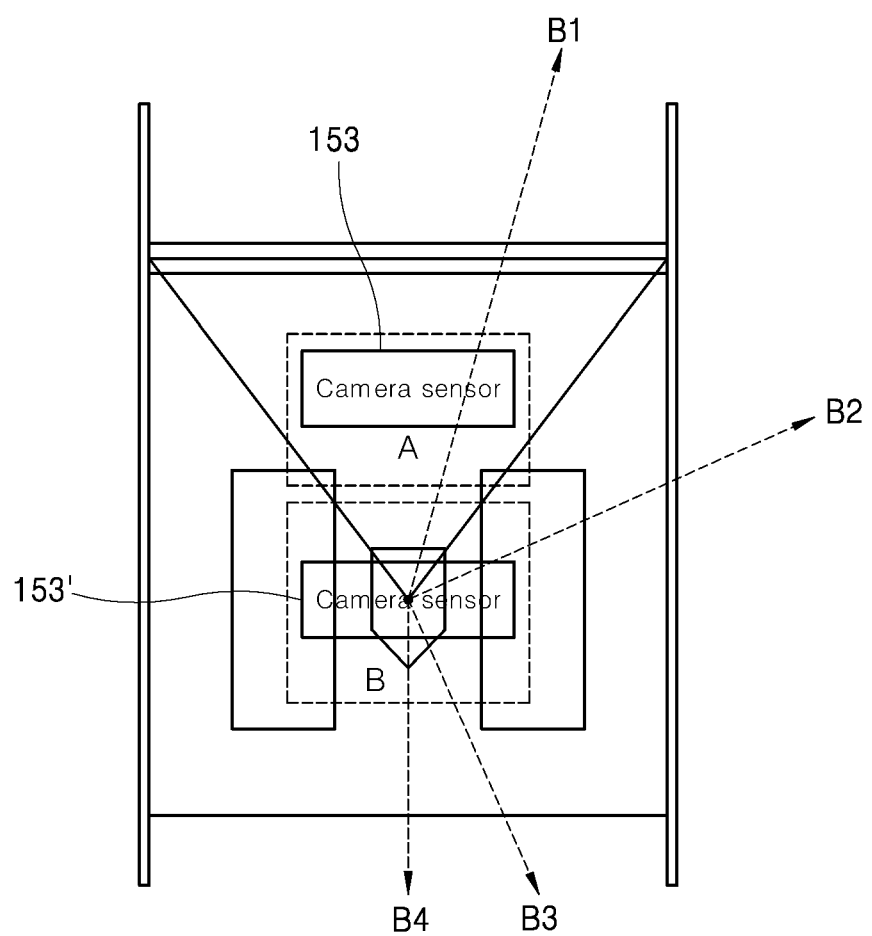

As shown in FIG. 5C, a camera sensor 153 is generally positioned at a location A slightly spaced apart from the batting point. However, shadow parts of the trajectories B2, B3, and B4 of the batted ball, which are not detected by the camera sensor 153, are caused.

In order to remove the shadow parts, according to the present invention, as shown in FIG. 5C, the position of the camera sensor 153 is set to a position B of a home plate where the batting point may be observed, thereby removing the shadow parts from the trajectories B2, B3, and B4 of the batted ball and detecting the change of the movement direction of the ball at the batting point, so that a rear foul tip can be distinguished (S143).

In general, the use of the camera sensor exponentially increases cost in proportion to the sensing power thereof. According to the present invention, the front detection sensor 151 is in charge of precisely determining the trajectory of the batted ball, and the camera sensor removes the shadow part from the trajectory of the batted ball. Accordingly, the use of the high-priced camera sensor is minimized.

As shown in FIG. 5D, the front detection sensor 151 is basically mounted at a position S1 where the ballpark makes contact with an extension line of a base, and may be mounted at a rear position S2 or a front position S3 of the position S1 according to the installation conditions of the present system.

In other words, as the front detection sensor 151 is closer to the batter box S3, the bat may pass through the sensor with gradually increasing probability. On the other hand, as the front detection sensor 151 is gradually away from the batter box S2, probability is gradually increased that the trajectory B5 of the batted ball bounced from the wall is measured as being identical to the trajectory B6 of the hit ball in terms of a sensor value.

In order to overcome the above limitation, the batting detection unit 150 removes error data occurring in bat recognition by placing the plane position sensor 152 and adjusting the position of the camera sensor 153, and distinguishes between the trajectory B5 of the foul ball bounced from a wall, a floor, or a ceil and the trajectory B6 of a hit ball.

The whole trajectory of the batted ball is read-out through the combination of all data detected by the front detection sensor 151, the plane position sensor 152, and the camera sensor 153 (S144).

Figure 7B:
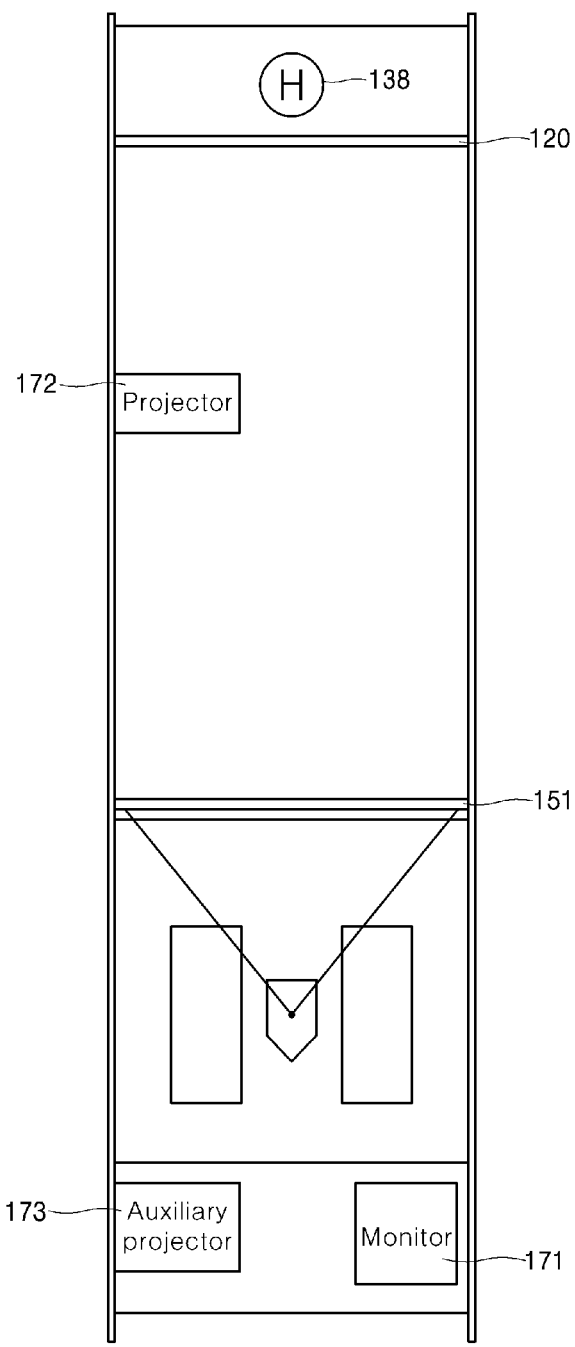

FIGS. 7A through 7C show views to explain the operation of a screen driving unit 170 in the screen baseball system shown in FIG. 1. The screen driving unit 170 includes a screen 120, a monitor 171, a projector 172, and an auxiliary projector 173.

FIG. 8 is a flowchart showing a part of an operation of a screen driving step (S150) in the playing method for the screen baseball system according to the present invention.

Hereinafter, the operation in the screen driving step in the screen baseball system according to the present invention will be described with reference to FIGS. 1 to 8.

Operation in Screen Driving Step

As shown in FIG. 7A, the screen 120 is mounted in front of the pitching machine 138. If the monitor 171 is commonly used with a management monitor of the game management unit 110, the position of the monitor 171 may be limited. Accordingly, the monitor 171 is mounted in a batter waiting room.

The projector 172 may be positioned at a rear of the batter boxy or at a proper distance (for example, 8 m) from the front of the screen 120 depending on the distance between the pitching machine and the batter box.

Although the same contents may be displayed on the screen 120 and the monitor 171, the screen 120 and the monitor 171 display mutually different contents according to the present invention. In detail, images similar to those of an actually broadcasted baseball game are displayed on the screen 120 through the projector 172 (S151), and the information (for example, information of a batter and the information of batting) required for progressing the game is intensively displayed on the monitor 171 (S152), so that users can be totally involved into the game.

As shown in FIG. 7B, when the pitching machine 138 is away from the batter box, the pitch machine 138 is away from the screen 120, the viewing angle of the batter may be narrowed.

In order to overcome this, according to the present invention, an auxiliary projector 173 is additionally mounted, so that surrounding images, which are not viewed on the screen 120, are displayed on a wall surface instead of the screen 120, so that the viewing angle of the batter is widened (S153).

In this case, as the surrounding images are displayed on the wall surface, image distortion may be caused according to a projection distance. Accordingly, the game management unit 110 corrects image distortion through an image distortion correcting software.

If a pitcher having the same appearance makes a pitching motion in pitching regardless of the distance between the screen 120 and the batter box, the batter may not feel reality resulting from a real distance. Accordingly, the game management unit 110 freely adjusts the shape of the pitcher so that the pitching motion is viewed with reality according to the distance between the screen 120 and the batter box (S154).

As shown in FIG. 7C, the screen 120 generally uses white fabric. However, if bright light exists on the rear surface of the screen 120, the image may not be clearly viewed.

In order to overcome this problem, according to the present invention, the rear light on the rear surface of the screen 120 is shield with a blind 121 (S155), and a reflective material is additionally coated on a front surface of the screen 120 in order to form a brighter screen (S156).

Figure 9A:
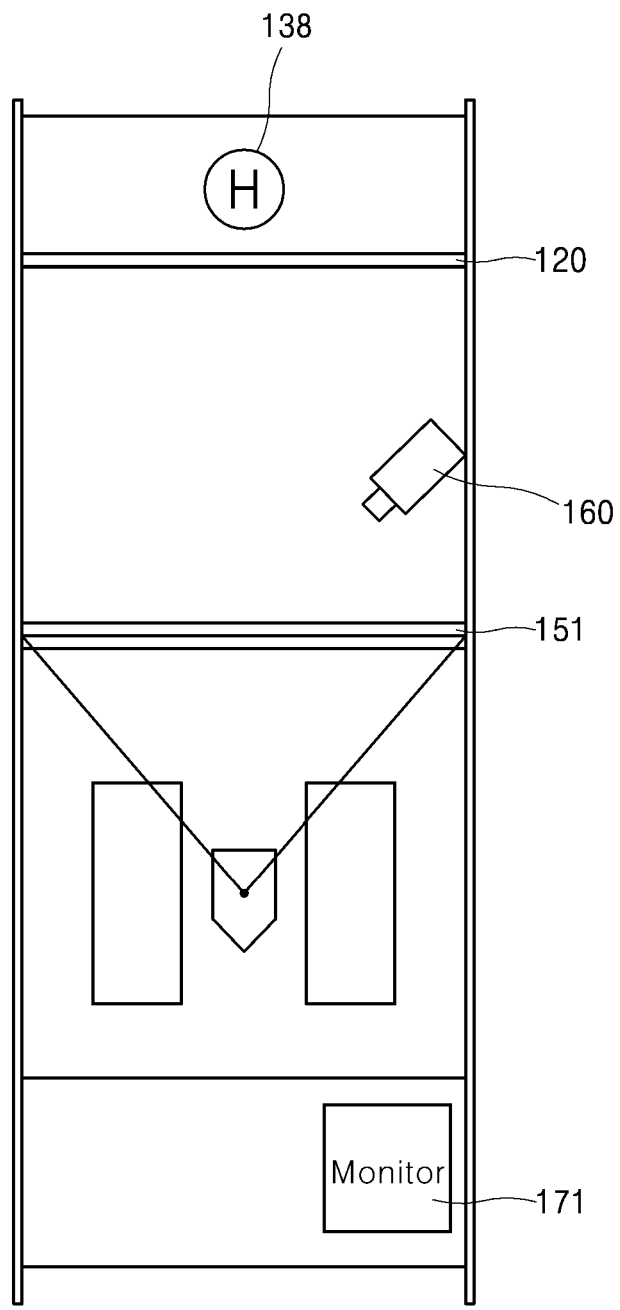
FIGS. 9A and 9B show views to explain the operation of a game photographing unit in the screen baseball system shown in FIG. 1.
Figure 9B:
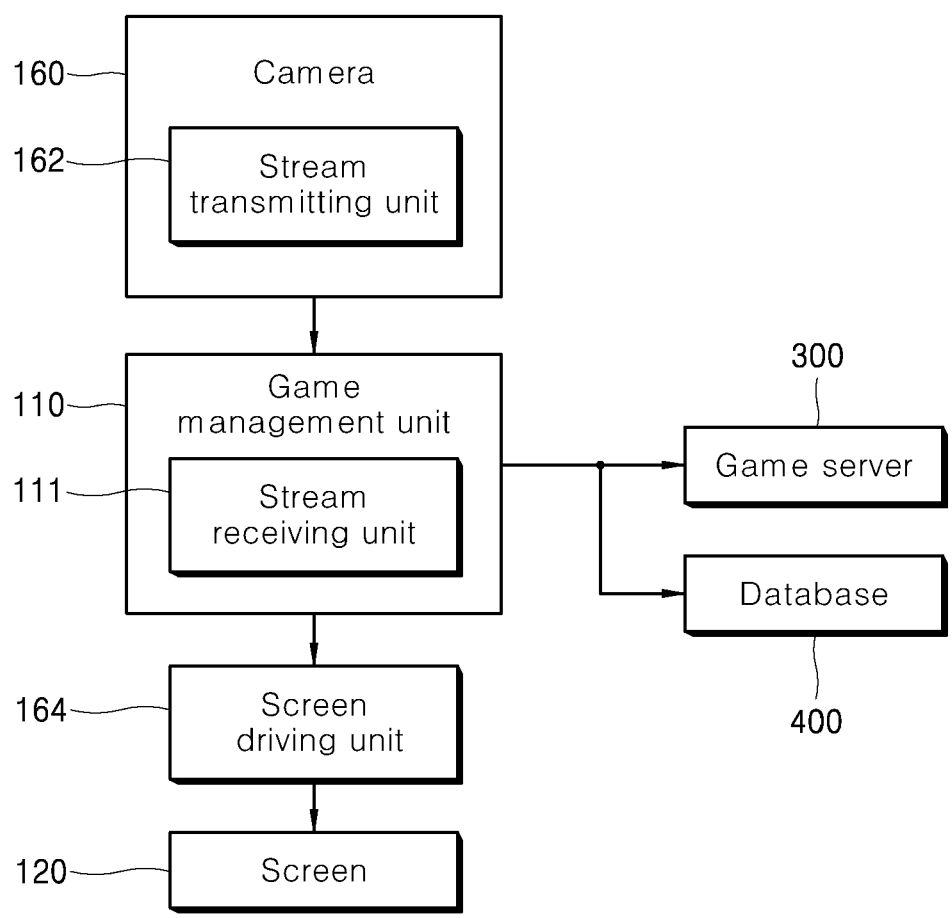

FIGS. 9A and 9B show views to explain the operation of a game photographing unit 160 in the screen baseball system shown in FIG. 1. The game photographing unit 160 includes a camera 160, a game management unit 110, a screen 120, a screen driving unit 170, a game server 300, and a database 400.

FIG. 10 is a flowchart showing a part of an operation of a screen driving step (S160) in the playing method for the screen baseball system according to the present invention.

The operation of the game photographing step in the screen baseball system according to the present invention will be described with reference to FIGS. 1 to 10.

Operation in Game Photographing Step

As shown in FIG. 9A, the camera 160 is mounted on the upper portion of the left wall or the right wall in front of the batter to photograph a batting image of the batter.

As shown in FIG. 9B, the camera 160 is embedded therein with a stream transmitting unit 162 to transmit the photographed batting image to the game management unit 110 (S161).

The game management unit 110 transmits the photographed batting image, which is received from the stream transmitting unit 162 through a stream receiving unit 111 embedded therein, to the screen driving unit 170 and reproduces the photographed batting image on the screen 120 (S162).

In addition, a specific image material, such as a good-quality hitting image, among the photographed batting images is temporarily stored, and transmitted and stored in the database 400. Thereafter, the specific image material may be utilized for the user training program and the character development program (S163).

For example, a user who wants to check a batting posture of the user to more improve a game capability may refer to the specific image material such as the hitting image on line through various schemes including the user training program, and may refer to the specific image material by displaying the specific image material on the screen.

In addition, the user may easily check advantages and disadvantages of the batting posture of the user by using the ball distribution obtained from the batting image and the game information.

Further, a user who wants a personal lesson to correct or complement the batting posture of the user is directly connected with an ex-player or a current player through the introduction of a shop by the character development program in order to receive the personal lesson from the ex-payer or the current player, thereby preventing users from avoiding a game match due to the physical superiority or the inferiority thereof.

As described above, according to the playing method for the screen baseball system of the present invention, an ordinary person can easily select a pitch of a ball to be pitched or various game conditions to freely enjoy baseball without a limitation such as the difference in level between users.

Further, factors to determine "strike" or "ball", options in various offensive and defensive actions, or a point calculating scheme can be variously adjusted beyond a game depending on batting. In addition, a ball is movable with reality along a predetermined trajectory according to pitching or batting in a virtual baseball field, so that the reality and interesting can be improved.

In addition, users may play a game even in mutually different regions by sharing the information of players and a game simulation in real time on line between regions geographically spaced apart from each other. Accordingly, the users can enjoy baseball without limitation in time and a space. The batting posture of the user is corrected through the character development program based on the batting images in the game and the game information, so that the user may improve a game capability.

Although a preferred embodiment of the present invention has been described for illustrative purposes, those skilled in the art will appreciate that various equivalents, modifications, additions and substitutions are possible, without departing from the scope and spirit of the invention as disclosed in the accompanying claims.

What is claimed is:

1. A playing method for a screen baseball system, the playing method comprises:
   (a) registering a personal rank by a computer;
   (b) transmitting pitching information to a pitching machine as a pitch type of a ball to be pitched is selected by a defense side user;
   (c) displaying a pitching motion on a screen responsively to a batter at an offense side pressing a pitching pedal, and starting a pitching action according to the selected pitch type by the pitching machine;
   (d) detecting a batting action of the batter by sensors and transmitting batting detection data to the computer;
   (e) receiving the batting detection data, converting the batting detection data into a trajectory of a batted ball, performing a simulation according to the trajectory of the batted ball, and displaying an image on the screen by the computer;
   (f) photographing a batting image of the batter and transmitting the batting image to the computer by a camera;
   (g) receiving batting image data and displayed simulation information and transmitting the batting image data and the simulation information to a game server and a database; and
   (h) storing the batting image and game information data by the database such that the batting image and the game information data are utilized for a user training program and a character development program.

2. The playing method of claim 1, further comprising (i) transmitting the simulation information and the batting image data, which are displayed, to a shop, where the defense side user is positioned, in real time by the game server to play a game on line, if the defense side user is another user positioned in a geographically remote region.

3. The playing method of claim 1, wherein the registering of the personal rank comprises:
   issuing a registration card having the personal rank and member subscription information of the batter; and
   registering the personal rank through a reader to read the registration card.

4. The method of claim 1, wherein the registering of the personal rank comprises:
   inputting the personal rank and member subscription information of the batter using an application of a portable terminal; and
   registering the personal rank together with the application through a short-range communication function of the portable terminal.

5. The playing method of claim 1, wherein the transmitting of the pitching information comprises selecting the pitch type of the ball to be pitched through a keypad or a joystick to prevent the pitching information from leaking to an offense side.

6. The playing method of claim 1, wherein (c) comprises:
   a pitch data calculation step of outputting a pitch value, which is created based on a preset value as the pitching information is received, a pitch value input into a keyboard or keypad or mouse or joystick, a pitch adjustment data corresponding to a strike zone based on information of a batter, and a posture adjustment data;
   a pitch adjustment step of receiving the pitch adjustment data to control a pitch driving unit and to adjust a pitch of a ball to be pitched; and
   a posture adjusting step of receiving the posture adjustment data to provide a control to adjust the pitching machine.

7. The playing method of claim 1, wherein the displaying of the pitching motion comprises determining the pitch type of the ball to be pitched depending on rotational speeds of three wheels by pitching machine having the three wheels pushing the ball by rotating forward.

8. The playing method of claim 1, wherein the displaying of the pitching motion comprises previously storing an adjustment value for a specific pitch into an embedded memory device of the pitching machine by considering that each shop of a plurality shops has a machine for pitching of a different revolution and a different distance between a machine for pitching and a batter box, wherein a certain shop of the plurality of shops is a shop having the pitching machine, and wherein the machine for pitching of the certain shop of the plurality of shops is the pitching machine.

9. The playing method of claim 1, wherein the detecting of the batting action comprises detecting coordinate data of the batted ball as a plurality of front detection sensors are mounted at a position where a ballpark makes contact with an extension line of a base, and at a front or a rear of the position;
   detecting a strike ball, which fails to be batted, and a foul ball as a plurality of plane position sensors are positioned at left and right batter boxes and a catcher region; and
   removing a shadow part from the trajectory of the batted ball and detecting change of a movement direction of the batted ball at a batting point as a camera sensor is mounted in a home plate region.

10. The playing method of claim 1, wherein the receiving of the batting detection data comprises manually adjusting a defensive position according to at least one of a batter characteristic, a runner situation, and a score situation by the defense side user; and
    manually adjusting a runner motion according to at least one of the runner situation and the score situation by an offense side.

11. The playing method of claim 1, wherein the receiving of the batting detection data comprises:
    displaying a broadcasted baseball image to represent a motion of a player on the screen through a projector;
    displaying information required for game progress on a monitor mounted in a batter waiting room; and
    displaying a surrounding image, which is not viewed on the screen, on a wall surface through an auxiliary projector.

12. The playing method of claim 1, wherein the receiving of the batting detection data comprises:
    freely adjusting an appearance of a pitcher depending on a distance between the screen and a batter box by the computer; and
    shielding light of a rear surface of the screen with a blind, and coating a reflective material on a front surface of the screen.

13. The playing method of claim 1, wherein the photographing and transmitting of the batting image of the batter comprise:
    transmitting the batting image of the batter from the camera;

reproducing the batting image on the screen; and temporarily storing the batting image, transmitting the batting image to the database if necessary, and utilizing the batting image for the user training program and the character development character.

14. The playing method of claim 1, wherein the receiving and the transmitting of the batting image data and the displayed simulation information are performed using one of a wired communication network, a short-range communication network, and an Internet network.

15. The playing method of claim 2, wherein the transmitting of the simulation information and the batting image data comprises:

inputting an available game schedule in an individual unit of a user or a team unit by the game server; and providing the available game schedule to the another user in a remote place.

* * * * *